United States Patent [19]

Mulder

[11] Patent Number: Plant 6,768

[45] Date of Patent: May 2, 1989

[54] DAHLIA PLANT NAMED CONNIE

[75] Inventor: Alle D. Mulder, Enkhuizen, Netherlands

[73] Assignee: Royal Sluis B.V., Enkhuizen, Netherlands

[21] Appl. No.: 131,370

[22] Filed: Dec. 10, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct Dahlia plant named Connie, having bright red-purple flower color, double flower form, dense foliage, continuous flowering, compact flower bouquet carried above the foliage, compact growth habit, and an adaptability to pot plant or natural outdoor cultures.

1 Drawing Sheet

The present invention relates to a new and distinct cultivar of Dahlia plant known by the cultivar name Connie, and botanically known as *Dahlia cav.*

Connie is a sport or mutation of a plant of the commercially well-known seed varieties of Dahlia marketed under the name Figaro. The sport was discovered by applicant in March, 1982 in Enkhuizen, The Netherlands.

The first act of asexual reproduction of Connie was accomplished when tuberous divisions were taken by me from the new cultivar after discovery in a controlled environment in Enkhuizen, The Netherlands. Subsequent horticultural examination of selected units has demonstrated that the combination of characteristics as herein disclosed for Connie are firmly fixed and are retained through successive generations of asexual reproduction.

Connie has not been observed under all possible environmental conditions. The phenotype may vary significantly with variations in environment such as temperature, light intensity, and day length. The following observations, measurements and comparisons describe plants grown in Enkhuizen, The Netherlands under greenhouse and outdoor conditions which approximate those generally used in commercial practice.

The following traits have been repeatedly observed and are determined to be basic characteristics of Connie, which in combination distinguish this Dahlia as a new and distinct cultivar:

(1) Intense, bright orange-red ray floret color.

(2) Double flower form.

(3) Dense foliage.

(4) Continuous flowering, with the flowers being carried above the foliage in a compact bouquet.

(5) Compact growth habit.

(6) Adaptable to pot plant culture as well as natural outdoor growth.

Relevant cultivars for comparison purposes are the seed varieties marketed under the name Rigoletto and the varieties of Figaro. In comparison to Rigoletto, Connie is more compact, has a double flower form, and bright orange-red ray floret color. Connie is distinguished from Figaro by its more compact habit, its earlier flowering, and its ray floret color.

The accompanying color photographic drawing shows typical inflorescence and foliage characteristics of Connie, with colors being as nearly true as possible with illustrations of this type. The photograph is a perspective view of several potted plants of Connie.

In the following description color references are made to The Royal Horticultural Society Colour Chart. The color values were determined at Enkhuizen, The Netherlands, and the characteristics noted below are based on plants grown at the same location.

Classification:

*Botanical.*—*Dahlia cav.* cv Connie (Group IV, peony flowered, classification of International Dahlia Register, 1969).

*Commercial.*—Dahlia.

Parentage: Sport of Figaro.

Plant:

*Form.*—Generally round.

*Size.*—Approximately 20 cm in height (from top of pot).

*Growth habit.*—Compact.

*Foliage.*—Size: Medium (according to Group classification noted above). Quantity: Abundant, dense. Color: Medium to dark green. Shape: Narrow, generally ovate, edges serrated. Texture: Relatively dull.

Flowers:

*Form.*—Double.

*Shape.*—Overall inflorescence is generally flat, with petals having blunt or slightly rounded tips.

*Size.*—Individual ray florets approximately 4 cm long and 2.5 cm wide; overall inflorescence approximately 8 cm in diameter.

*Borne.*—On pedicals which are approximately 7–8 cm in length; top of the pedicel oriented at approximately 120° to the vertical axis of the plant; flowers carried compactly above the foliage.

*Quantity.*—Floriferous.

*Continuity.*—Continuously flowers outdoors after first flower opens.

*Stems.*—Color of both new stem and flowering stem is light green with anthocyanin coloration.

*Color.*—Fully open, upper surface 43A. Fully open, under surface 43B. Half open, upper surface 40A. Half open, under surface 40B.

*Reproductive organs.*—Normal.

I claim:

1. A new and distinct cultivar of Dahlia plant named Connie, as illustrated and described.

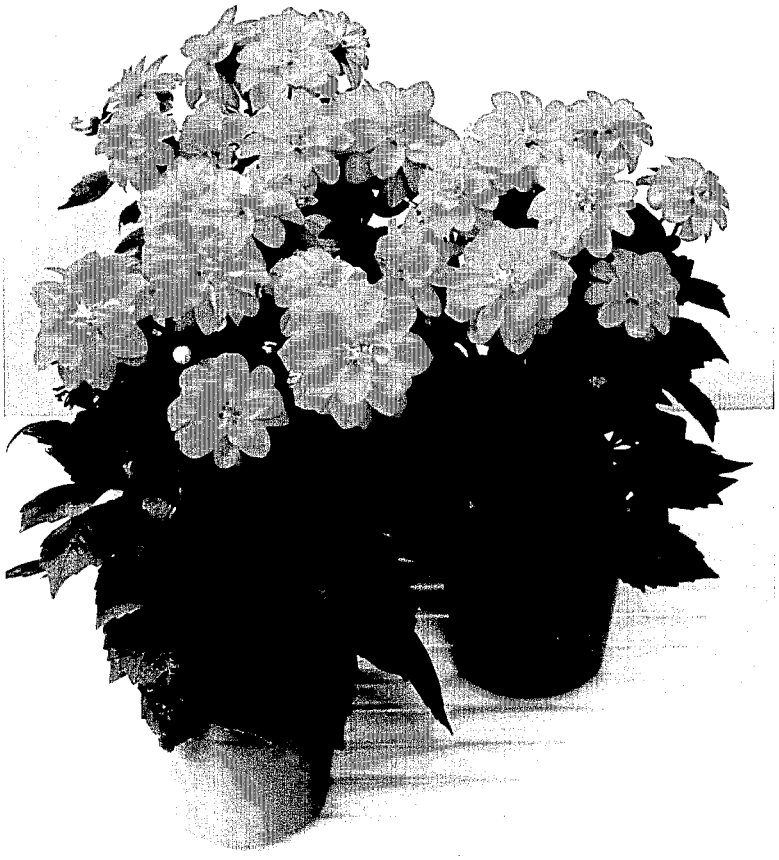

* * * * *